(12) United States Patent
Chen (10) Patent No.: US 9,168,369 B2
(45) Date of Patent: *Oct. 27, 2015

(54) ELECTRODE ARRAY HAVING A RAIL SYSTEM AND METHODS OF MANUFACTURING THE SAME

(71) Applicant: BOSTON SCIENTIFIC NEUROMODULATION CORPORATION, Valencia, CA (US)

(72) Inventor: Roger Chen, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/335,777

(22) Filed: Jul. 18, 2014

(65) Prior Publication Data

US 2015/0073517 A1 Mar. 12, 2015

Related U.S. Application Data

(63) Continuation of application No. 12/946,659, filed on Nov. 15, 2010, now Pat. No. 8,788,063.

(60) Provisional application No. 61/265,254, filed on Nov. 30, 2009.

(51) Int. Cl.
*A61N 1/00* (2006.01)
*A61N 1/05* (2006.01)

(52) U.S. Cl.
CPC .......... *A61N 1/0534* (2013.01); *Y10T 29/49117* (2015.01)

(58) Field of Classification Search
CPC . A61N 1/0534; A61N 1/0424; A61N 1/0529; A61N 1/0539; A61N 1/0476
See application file for complete search history.

(56) References Cited

U.S. PATENT DOCUMENTS

| 4,602,624 A | 7/1986 | Naples et al. |
|---|---|---|
| 4,630,611 A | 12/1986 | King |
| 4,744,370 A | 5/1988 | Harris |
| 5,000,194 A | 3/1991 | van den Honert et al. |

(Continued)

FOREIGN PATENT DOCUMENTS

| EP | 0580928 A1 | 2/1994 |
|---|---|---|
| EP | 0650694 B1 | 7/1998 |

(Continued)

OTHER PUBLICATIONS

U.S. Appl. No. 14/286,940, filed May 23, 2014.

(Continued)

*Primary Examiner* — Michael Kahelin
*Assistant Examiner* — Mallika D Fairchild
(74) *Attorney, Agent, or Firm* — Lowe Graham Jones PLLC; Bruce E. Black (57) ABSTRACT

A device for brain stimulation includes a lead having a longitudinal surface and a distal end. The lead includes a longitudinal rail disposed within the distal end of the lead. The longitudinal rail includes at least two prongs, each prong being configured and arranged to receive at least one segmented electrode. The lead further includes a plurality of segmented electrodes disposed along the longitudinal surface of the lead near the distal end of the lead. Each of the plurality of segmented electrodes is coupled to one of the at least two prongs of the rail.

20 Claims, 10 Drawing Sheets

(56) References Cited

U.S. PATENT DOCUMENTS

| | | |
|---|---|---|
| 5,135,001 A | 8/1992 | Sinofsky et al. |
| 5,374,285 A | 12/1994 | Vaiani et al. |
| 5,458,629 A | 10/1995 | Baudino et al. |
| 5,522,874 A | 6/1996 | Gates |
| 5,711,316 A | 1/1998 | Elsberry et al. |
| 5,713,922 A | 2/1998 | King |
| 5,800,350 A | 9/1998 | Coppleson et al. |
| 5,843,148 A | 12/1998 | Gijsbers et al. |
| 5,938,688 A | 8/1999 | Schiff |
| 5,987,361 A | 11/1999 | Mortimer |
| 6,018,684 A | 1/2000 | Bartig et al. |
| 6,134,478 A | 10/2000 | Spehr |
| 6,161,047 A | 12/2000 | King et al. |
| 6,167,311 A | 12/2000 | Rezai |
| 6,322,559 B1 | 11/2001 | Daulton et al. |
| 6,510,347 B2 | 1/2003 | Borkan |
| 6,556,873 B1 | 4/2003 | Smits |
| 6,564,078 B1 | 5/2003 | Marino et al. |
| 6,678,564 B2 | 1/2004 | Ketterl et al. |
| 6,757,970 B1 | 7/2004 | Kuzma et al. |
| 7,027,852 B2 | 4/2006 | Helland |
| 7,047,084 B2 | 5/2006 | Erickson et al. |
| 7,292,890 B2 | 11/2007 | Whitehurst et al. |
| 7,489,971 B1 | 2/2009 | Franz |
| 7,668,601 B2 | 2/2010 | Hegland et al. |
| 7,761,985 B2 | 7/2010 | Hegland et al. |
| 7,809,446 B2 | 10/2010 | Meadows |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,974,705 B2 | 7/2011 | Zdeblick et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,099,177 B2 | 1/2012 | Dahlberg |
| 8,225,504 B2 | 7/2012 | Dye et al. |
| 8,295,944 B2 | 10/2012 | Howard et al. |
| 8,321,025 B2 | 11/2012 | Bedenbaugh |
| 8,391,985 B2 | 3/2013 | McDonald |
| 8,583,237 B2 | 11/2013 | Bedenbaugh |
| 2002/0156513 A1 | 10/2002 | Borkan |
| 2002/0183817 A1 | 12/2002 | Van Venrooij et al. |
| 2005/0015130 A1 | 1/2005 | Gill |
| 2005/0038489 A1 | 2/2005 | Grill |
| 2005/0171587 A1 | 8/2005 | Daglow et al. |
| 2006/0025841 A1 | 2/2006 | McIntyre |
| 2006/0247697 A1 | 11/2006 | Sharma et al. |
| 2007/0203546 A1 | 8/2007 | Stone et al. |
| 2008/0103580 A1 | 5/2008 | Gerber |
| 2008/0114230 A1 | 5/2008 | Addis |
| 2008/0215125 A1 | 9/2008 | Farah et al. |
| 2009/0204192 A1 | 8/2009 | Carlton et al. |
| 2010/0030298 A1 | 2/2010 | Martens et al. |
| 2010/0036468 A1 | 2/2010 | Decre et al. |
| 2010/0076535 A1 | 3/2010 | Pianca et al. |
| 2010/0082076 A1 | 4/2010 | Lee et al. |
| 2010/0094387 A1 | 4/2010 | Pianca et al. |
| 2010/0268298 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0005069 A1 | 1/2011 | Pianca |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0238129 A1 | 9/2011 | Moffitt et al. |
| 2011/0245903 A1 | 10/2011 | Schulte et al. |
| 2011/0301665 A1 | 12/2011 | Mercanzini et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2013/0109254 A1 | 5/2013 | Klardie et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0317587 A1 | 11/2013 | Barker |
| 2013/0325091 A1 | 12/2013 | Pianca et al. |
| 2014/0039587 A1 | 2/2014 | Romero |
| 2014/0039590 A1 | 2/2014 | Moffitt et al. |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 9732628 A1 | 9/1997 |
| WO | 9955411 A3 | 2/2000 |
| WO | 0038574 A1 | 7/2000 |
| WO | 0158520 A1 | 8/2001 |
| WO | 02068042 A1 | 9/2002 |
| WO | 2004045707 A1 | 6/2004 |
| WO | 2008018067 A2 | 2/2008 |
| WO | 2008053789 A1 | 5/2008 |
| WO | 2009025816 A1 | 2/2009 |
| WO | 2009102536 A1 | 8/2009 |
| WO | 2013162775 A2 | 10/2013 |
| WO | 2014018092 A1 | 1/2014 |

OTHER PUBLICATIONS

U.S. Appl. No. 14/286,889, filed May 23, 2014.
U.S. Appl. No. 14/286,934, filed May 23, 2014.
U.S. Appl. No. 14/325,249, filed Jul. 7, 2014.
U.S. Appl. No. 14/332,212, filed Jul. 15, 2014.
U.S. Appl. No. 14/452,461, filed Aug. 5, 2014.
U.S. Appl. No. 14/286,829, filed May 23, 2014.
U.S. Appl. No. 14/469,214, filed Aug. 26, 2014.
U.S. Appl. No. 14/286,797, filed May 23, 2014.
U.S. Appl. No. 14/557,211, filed Dec. 1, 2014.
Official Communication for U.S. Appl. No. 12/946,659 mailed May 8, 2012.
Official Communication for U.S. Appl. No. 12/946,659 mailed Nov. 29, 2012.

ELECTRODE ARRAY HAVING A RAIL SYSTEM AND METHODS OF MANUFACTURING THE SAME

CROSS-REFERENCE TO RELATED APPLICATIONS

This application is a continuation of U.S. patent application Ser. No. 12/946,659 filed Nov. 15, 2010 which claims the benefit under 35 U.S.C. §119(e) of U.S. Provisional Patent Application Ser. No. 61/265,254 filed on Nov. 30, 2009, all of which are incorporated herein by reference.

FIELD

The invention is directed to devices and methods for brain stimulation including deep brain stimulation. In addition, the invention is directed to devices and method for brain stimulation using a lead having a plurality of segmented electrodes coupled to a rail.

BACKGROUND

Deep brain stimulation can be useful for treating a variety of conditions including, for example, Parkinson's disease, dystonia, essential tremor, chronic pain, Huntington's Disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging (MRI) or computerized tomography (CT) scans can provide a starting point for determining where the stimulating electrode should be positioned to provide the desired stimulus to the target neurons.

Upon insertion, current is introduced along the length of the lead to stimulate target neurons in the brain. This stimulation is provided by electrodes, typically in the form of rings, disposed on the lead. The current projects from each electrode similarly and in all directions at any given length along the axis of the lead. Because of the shape of the electrodes, radial selectivity of the current is minimal. This results in the unwanted stimulation of neighboring neural tissue, undesired side effects and an increased duration of time for the proper therapeutic effect to be obtained.

In the field of deep brain stimulation, radially segmented electrode arrays (RSEA) have been developed to provide superior radial selectivity of current. Radially segmented electrode arrays are useful for deep brain stimulation because the target structures in the deep brain are often not symmetric about the axis of the distal electrode array. In some cases, a target may be located on one side of a plane running through the axis of the lead. In other cases, a target may be located at a plane that is offset at some angle from the axis of the lead. Thus, radially segmented electrode arrays may be useful for selectively simulating tissue. Radially segmented arrays may be made using a central rail upon which the segmented electrodes are disposed.

BRIEF SUMMARY

In one embodiment, a device for brain stimulation includes a lead having a longitudinal surface and a distal end. The lead includes a longitudinal rail disposed within the distal end of the lead. The longitudinal rail includes at least two prongs, each prong being configured and arranged to receive at least one segmented electrode. The lead further includes a plurality of segmented electrodes disposed along the longitudinal surface of the lead near the distal end of the lead. Each of the plurality of segmented electrodes is coupled to one of the at least two prongs of the rail.

In another embodiment, a device for brain stimulation includes a lead having a longitudinal surface and a distal end. The lead includes a longitudinal rail disposed within the distal end of the lead. The longitudinal rail includes at least two prongs for receiving at least one segmented electrode. The lead further includes a plurality of segmented electrodes disposed along the longitudinal surface of the lead near the distal end of the lead. The plurality of segmented electrodes are configured and arranged to couple to the prongs of the rail.

In yet another embodiment, a method of manufacturing a device for brain stimulation includes forming a longitudinal rail having at least two prongs. Each prong is configured and arranged to receive a plurality of segmented electrodes. A plurality of segmented electrodes are coupled to the rail. The plurality of segmented electrodes are configured and arranged to couple to the at least two prongs of the rail. At least one set of spacers is introduced at a predetermined longitudinal level along the length of the rail. Each set of spacers is configured and arranged to divide the plurality of segmented electrodes into different longitudinal levels. A substantially cylindrical lead body is formed. The substantially cylindrical lead body is configured to at least partially surround the longitudinal rail, the plurality of segmented electrodes and the at least one set of spacers.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of devices and methods for brain stimulation including deep brain stimulation. In addition, the invention is directed to devices and method for brain stimulation using a lead having a plurality of segmented electrodes and a rail.

A lead for deep brain stimulation may include stimulation electrodes, recording electrodes, or a combination of both. A practitioner may determine the position of the target neurons using the recording electrode(s) and then position the stimulation electrode(s) accordingly without removal of a recording lead and insertion of a stimulation lead. In some embodiments, the same electrodes can be used for both recording and stimulation. In some embodiments, separate leads can be used; one with recording electrodes which identify target neurons, and a second lead with stimulation electrodes that replaces the first after target neuron identification. A lead may include recording electrodes spaced around the circumference of the lead to more precisely determine the position of the target neurons. In at least some embodiments, the lead is rotatable so that the stimulation electrodes can be aligned with the target neurons after the neurons have been located using the recording electrodes.

Deep brain stimulation devices and leads are described in the art. See, for instance, U.S. Patent Publication 2006/0149335 A1 ("Devices and Methods For Brain Stimulation"), and co-pending patent application U.S. Ser. No. 12/237,888 ("Leads With Non-Circular-Shaped Distal Ends For Brain Stimulation Systems and Methods of Making and Using"). Each of these references is incorporated herein by reference in its respective entirety.

Figure 10:
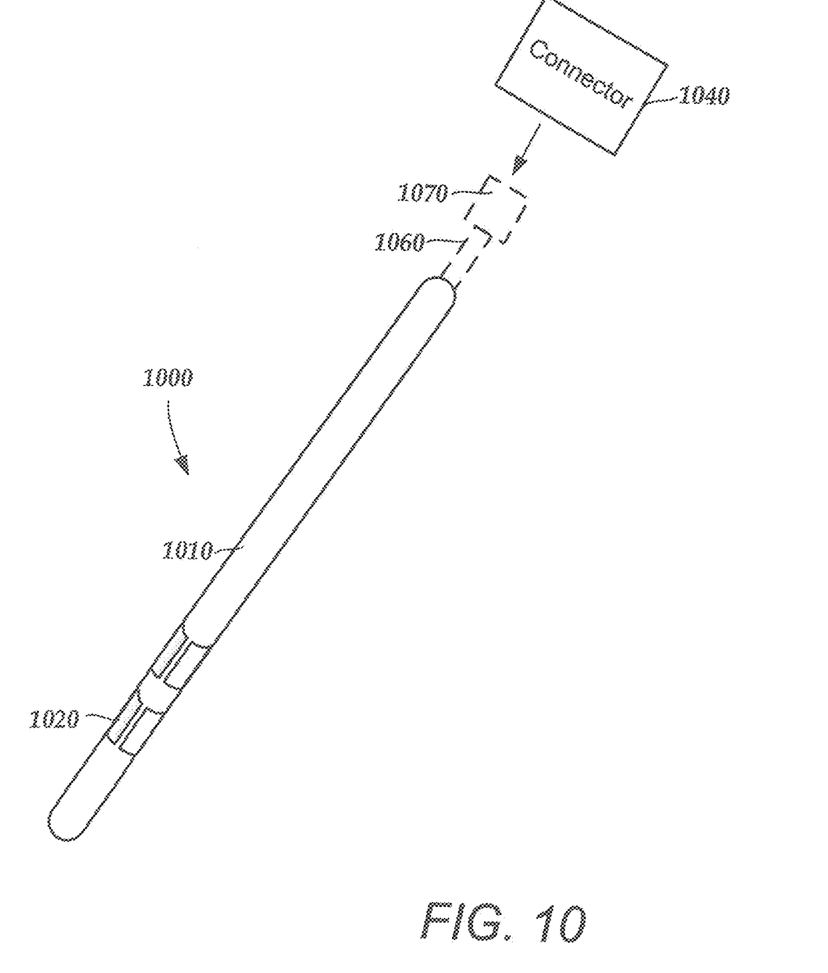
FIG. 10 is a schematic side view of one embodiment of a device for brain stimulation, according to the invention.

FIG. 10 illustrates one embodiment of a device 1000 for brain stimulation. The device includes a lead 1010, segmented electrodes 1020, a connector 1040 for connection of the electrodes to a control unit, and a stylet 1060 for assisting in insertion and positioning of the lead in the patient's brain. The stylet 1060 can be made of a rigid material. Examples of suitable materials include tungsten, stainless steel, or plastic. The stylet 1060 may have a handle 1070 to assist insertion into the lead, as well as rotation of the stylet and lead. The connector 1040 fits over the proximal end of the lead 1010, preferably after removal of the stylet 1060.

In one example of operation, access to the desired position in the brain can be accomplished by drilling a hole in the patient's skull or cranium with a cranial drill (commonly referred to as a burr), and coagulating and incising the dura mater, or brain covering. The lead 1010 can be inserted into the cranium and brain tissue with the assistance of the stylet 1060. The lead can be guided to the target location within the brain using, for example, a stereotactic frame and a microdrive motor system. In some embodiments, the microdrive motor system can be fully or partially automatic. The microdrive motor system may be configured to perform one or more of the following actions (alone or in combination): rotate the lead, insert the lead, or retract the lead. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

It will be understood that the lead 1010 for deep brain stimulation can include stimulation electrodes, recording electrodes, or both. In at least some embodiments, the lead is rotatable so that the stimulation electrodes can be aligned with the target neurons after the neurons have been located using the recording electrodes.

Stimulation electrodes may be disposed on the circumference of the lead to stimulate the target neurons. Stimulation electrodes may be ring-shaped so that current projects from each electrode equally in every direction at any given length along the axis of the lead. To achieve current steering, segmented electrodes can be utilized additionally or alternatively. Though the following description discusses stimulation electrodes, it will be understood that all configurations of the stimulation electrodes discussed may be utilized in arranging recording electrodes as well.

Figure 1A:
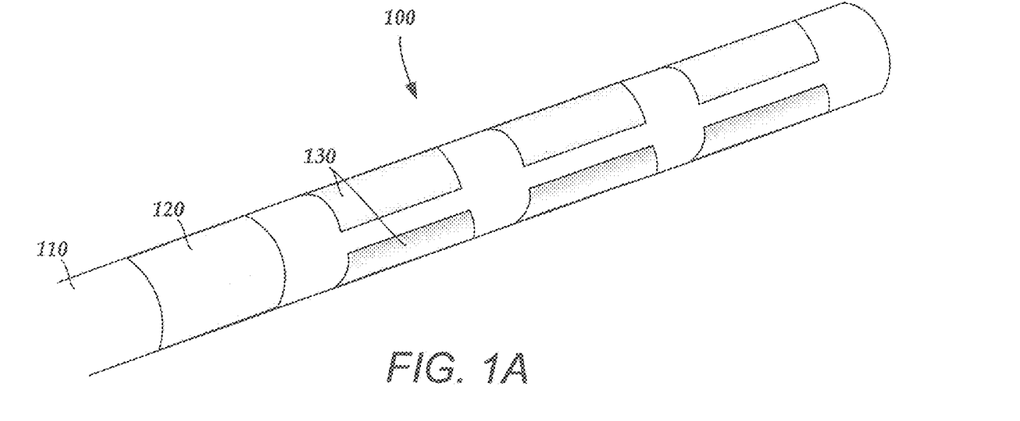
FIG. 1A is a schematic perspective view of one embodiment of a portion of a lead having a plurality of segmented electrodes and a ring electrode, according to the invention.

FIG. 1A illustrates one embodiment of a lead 100 for brain stimulation. The device includes a lead body 110, one or more ring electrodes 120, and a plurality of segmented electrodes 130. The lead body 110 can be formed of a biocompatible, non-conducting material such as, for example, a polymeric material. Suitable polymeric materials include, but are not limited to, silicone, polyethylene, polyurethanes, polyureas, or polyurethane-ureas. In at least some instances, the lead may be in contact with body tissue for extended periods of time. In at least some embodiments, the lead has a cross-sectional diameter of no more than 1.5 mm and may be in the range of 0.75 to 1.5 mm. In at least some embodiments, the lead has a length of at least 10 cm and the length of the lead may be in the range of 25 to 70 cm.

Stimulation electrodes may be disposed on the lead body 110. These stimulation electrodes may be made using a metal, alloy, conductive oxide, or any other suitable conductive material. Examples of suitable materials include, but are not limited to, platinum, iridium, platinum iridium alloy, stainless steel, titanium, or tungsten. Preferably, the stimulation electrodes are made of a material that is biocompatible and does not substantially corrode under expected operating conditions in the operating environment for the expected duration of use.

In at least some embodiments, any of the electrodes can be used as an anode or cathode and carry anodic or cathodic current. In some instances, an electrode might be an anode for a period of time and a cathode for a period of time. In other embodiments, the identity of a particular electrode or electrodes as an anode or cathode might be fixed.

The lead contains a plurality of segmented electrodes 130. Any number of segmented electrodes 130 may be disposed on the lead body 110. In some embodiments, the segmented electrodes 130 are grouped in sets of segmented electrodes, each set disposed around the circumference of the lead at or near a particular longitudinal position. The lead may have any number of sets of segmented electrodes. In at least some embodiments, the lead has one, two, three, four, five, six, seven, or eight sets of segmented electrodes. In at least some embodiments, each set of segmented electrodes contains the same number of segmented electrodes 130. In some embodiments, each set of segmented electrodes contains three segmented electrodes 130. In at least some other embodiments, each set of segmented electrodes contains two, four, five, six, seven or eight segmented electrodes. The segmented electrodes 130 may vary in size and shape. In some embodiments, the segmented electrodes 130 are all of the same size, shape, diameter, width or area or any combination thereof. In some embodiments, the segmented electrodes of each set (or even all segmented electrodes) may be identical in size and shape.

In at least some embodiments, each set of segmented electrodes 130 may be disposed around the circumference of the lead body 110 to form a substantially or approximately cylindrical shape around the lead body 110. The spacing of the segmented electrodes 130 around the circumference of the lead body 110 may vary. In at least some embodiments, equal spaces, gaps or cutouts are disposed between each segmented electrodes 130 around the circumference of the lead body 110. In other embodiments, the spaces, gaps or cutouts between segmented electrodes may differ in size or shape. In other embodiments, the spaces, gaps, or cutouts between segmented electrodes may be uniform for a particular set of segmented electrodes or for all sets of segmented electrodes. The segmented electrodes 130 may be positioned in irregular or regular intervals around the lead body 110.

Stimulation electrodes in the form of ring electrodes 120 may be disposed on any part of the lead body 110, usually near a distal end of the lead. FIG. 1A illustrates a portion of a lead having one ring electrode. Any number of ring electrodes, may be disposed along the length of the lead body 110. For example, the lead body may have one ring electrode, two ring electrodes, three ring electrodes or four ring electrodes. In some embodiments, the lead will have five, six, seven or eight ring electrodes. Other embodiments do not include ring electrodes.

In some embodiments, the ring electrodes 120 are substantially cylindrical and wrap around the entire circumference of the lead body 110. In some embodiments, the outer diameter of the ring electrodes 120 is substantially equal to the outer diameter of the lead body 110. Furthermore, the width of ring electrodes 120 may vary according to the desired treatment and the location of the target neurons. In some embodiments the width of the ring electrode 120 is less than or equal to the diameter of the ring electrode 120. In other embodiments, the width of the ring electrode 120 is greater than the diameter of the ring electrode 120.

Conductors (not shown) that attach to or from the ring electrodes 120 and segmented electrodes 130 also pass through the lead body 110. These conductors may pass through the material of the lead or through a lumen defined by the lead. The conductors are presented at a connector for coupling of the electrodes to a control unit (not shown). In one embodiment, the stimulation electrodes correspond to wire conductors that extend out of the lead body 110 and are then trimmed or ground down flush with the lead surface. The conductors may be coupled to a control unit to provide stimulation signals, often in the form of pulses, to the stimulation electrodes.

Figure 1B:
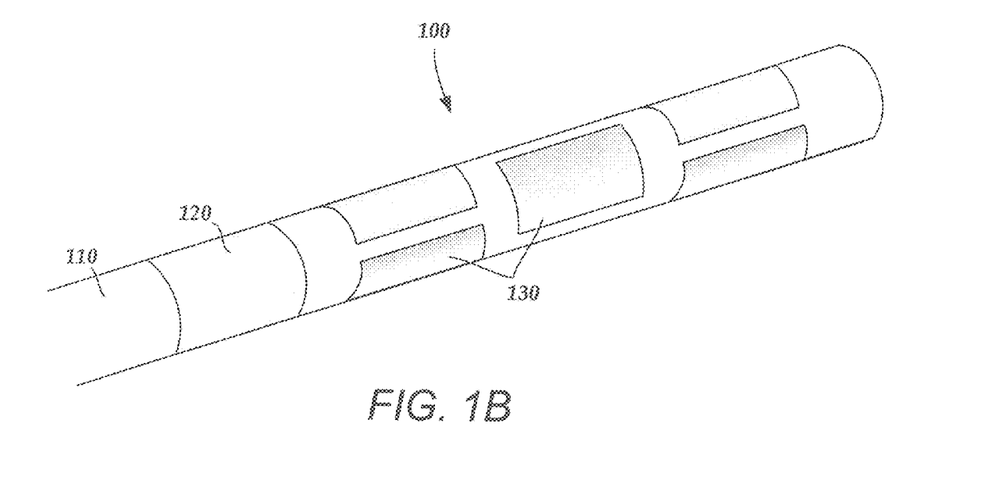
FIG. 1B is a schematic perspective view of another embodiment of a lead having a plurality of segmented electrodes arranged in staggered orientation, according to the invention.

FIG. 1B is a schematic perspective view of another embodiment of a lead having a plurality of segmented electrodes. As seen in FIG. 1B, the plurality of segmented electrodes 130 may be arranged in different orientations relative to each other. In contrast to FIG. 1A, where the two sets of segmented electrodes are aligned along the length of the lead body 110, FIG. 1B displays another embodiment in which the two sets of segmented electrodes 130 are staggered. In at least some embodiments, the sets of segmented electrodes are staggered such that no segmented electrodes are aligned along the length of the lead body 110. In some embodiments, the segmented electrodes may be staggered so that at least one of the segmented electrodes is aligned with another segmented electrode of a different set, and the other segmented electrodes are not aligned.

Any number of segmented electrodes 130 may be disposed on the lead body 110 in any number of sets. FIGS. 1A and 1B illustrate embodiments including three sets of segmented electrodes. These three sets of segmented electrodes 130 may be disposed in different configurations. For example, three sets of segmented electrodes 130 may be disposed on the distal end of the lead body 110, distal to the ring electrode 120. Alternatively, three sets of segmented electrodes 130 may be disposed proximal to the ring electrode 120. By varying the location of the segmented electrodes 130, different coverage of the target neurons may be selected. For example, a specific configuration may be useful if the physician anticipates that the neural target will be closer to the distal tip of the lead body 110, while another arrangement may be useful if the physician anticipates that the neural target will be closer to the proximal end of the lead body 110. In at least some embodiments, the ring electrodes 120 alternate with sets of segmented electrodes 130.

Any combination of ring electrodes 120 and segmented electrodes 130 may be disposed on the lead. In some embodiments the segmented electrodes are arranged in sets. For example, a lead may include a first ring electrode 120, two sets of segmented electrodes, each set formed of three segmented electrodes 130, and a final ring electrode 120 at the end of the lead. This configuration may simply be referred to as a 1-3-3-1 configuration. It may be useful to refer to the electrodes with this shorthand notation. Other eight electrode configurations include, for example, a 2-2-2-2 configuration, where four sets of segmented electrodes are disposed on the lead, and a 4-4 configuration, where two sets of segmented electrodes, each having four segmented electrodes 130 are disposed on the lead. In some embodiments, the lead will have 16 electrodes. Possible configurations for a 16-electrode lead include, but are not limited to 4-4-4-4, 8-8, 3-3-3-3-3-1 (and all rearrangements of this configuration), and 2-2-2-2-2-2-2-2.

Figure 2:
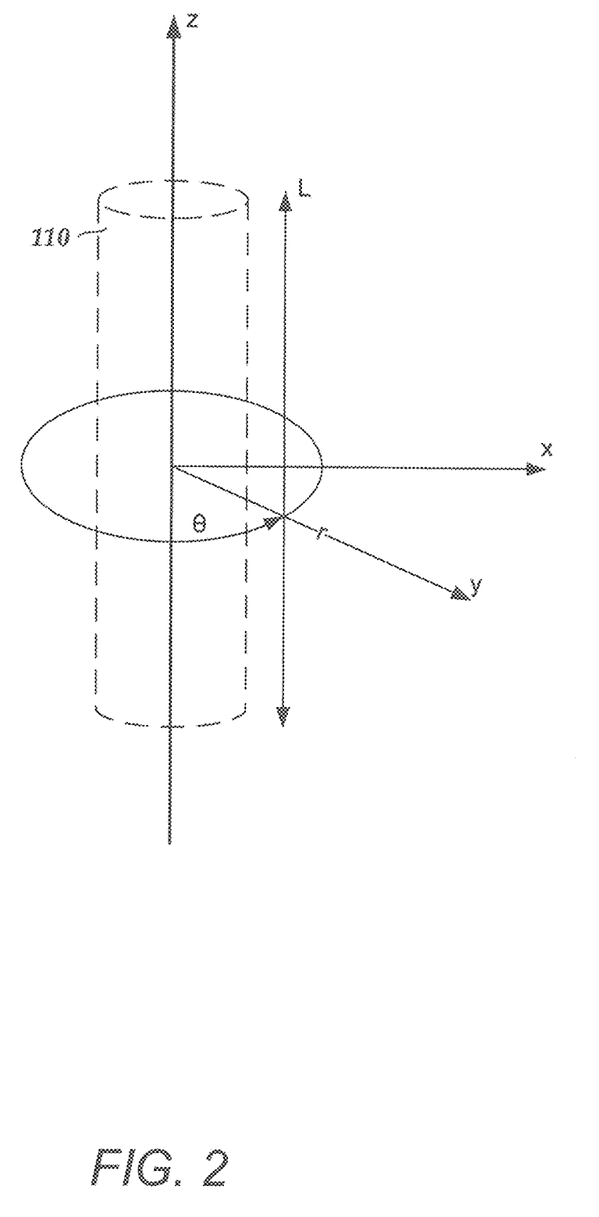
FIG. 2 is a schematic diagram of radial current steering along various electrode levels along the length of a lead, according to the invention.

FIG. 2 is a schematic diagram to illustrate radial current steering along various electrode levels along the length of a lead. While conventional lead configurations with ring electrodes are only able to steer current along the length of the lead (the z-axis), the segmented electrode configuration is capable of steering current in the x-axis, y-axis as well as the z-axis. Thus, the centroid of stimulation may be steered in any direction in the three-dimensional space surrounding the lead body 110. In some embodiments, the radial distance, r, and the angle θ around the circumference of the lead body 110 may be dictated by the percentage of anodic current (recognizing that stimulation predominantly occurs near the cathode, although strong anodes may cause stimulation as well) introduced to each electrode as will be described in greater detail below. In at least some embodiments, the configuration of anodes and cathodes along the segmented electrodes 130 allows the centroid of stimulation to be shifted to a variety of different locations along the lead body 110.

As can be appreciated from FIG. 2, the centroid of stimulation can be shifted at each level along the length of the lead. The use of multiple sets of segmented electrodes 130 at different levels along the length of the lead allows for three-dimensional current steering. In some embodiments, the sets of segmented electrodes 130 are shifted collectively (i.e. the centroid of simulation is similar at each level along the length of the lead). In at least some other embodiments, each set of segmented electrodes 130 is controlled independently. Each set of segmented electrodes may contain two, three, four, five, six, seven, eight or more segmented electrodes. It will be understood that different stimulation profiles may be produced by varying the number of segmented electrodes at each level. For example, when each set of segmented electrodes includes only two segmented electrodes, uniformly distributed gaps (inability to stimulate selectively) may be formed in the stimulation profile. In some embodiments, at least three segmented electrodes 130 are utilized to allow for true 360° selectivity.

In addition to 360° selectivity, a lead having segmented electrodes may provide several advantages. First, the lead may provide for more directed stimulation, as well as less "wasted" stimulation (i.e. stimulation of regions other than the target region). By directing stimulation toward the target tissue, side effects may be reduced. Furthermore, because stimulation is directed toward the target site, the battery in an implantable pulse generator may last for a longer period of time between recharging.

As previously indicated, the foregoing configurations may also be used while utilizing recording electrodes. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

Radially segmented electrode arrays may be manufactured in a variety of ways. In at least some embodiments, a rail disposed within the lead is used to position and properly attach the segmented electrodes. The rail system may be modified to utilize different numbers of segmented electrodes, to adjust the radial spacing between segmented electrodes or to include spacers to vary the longitudinal position between levels of segmented electrodes.

Figure 3:
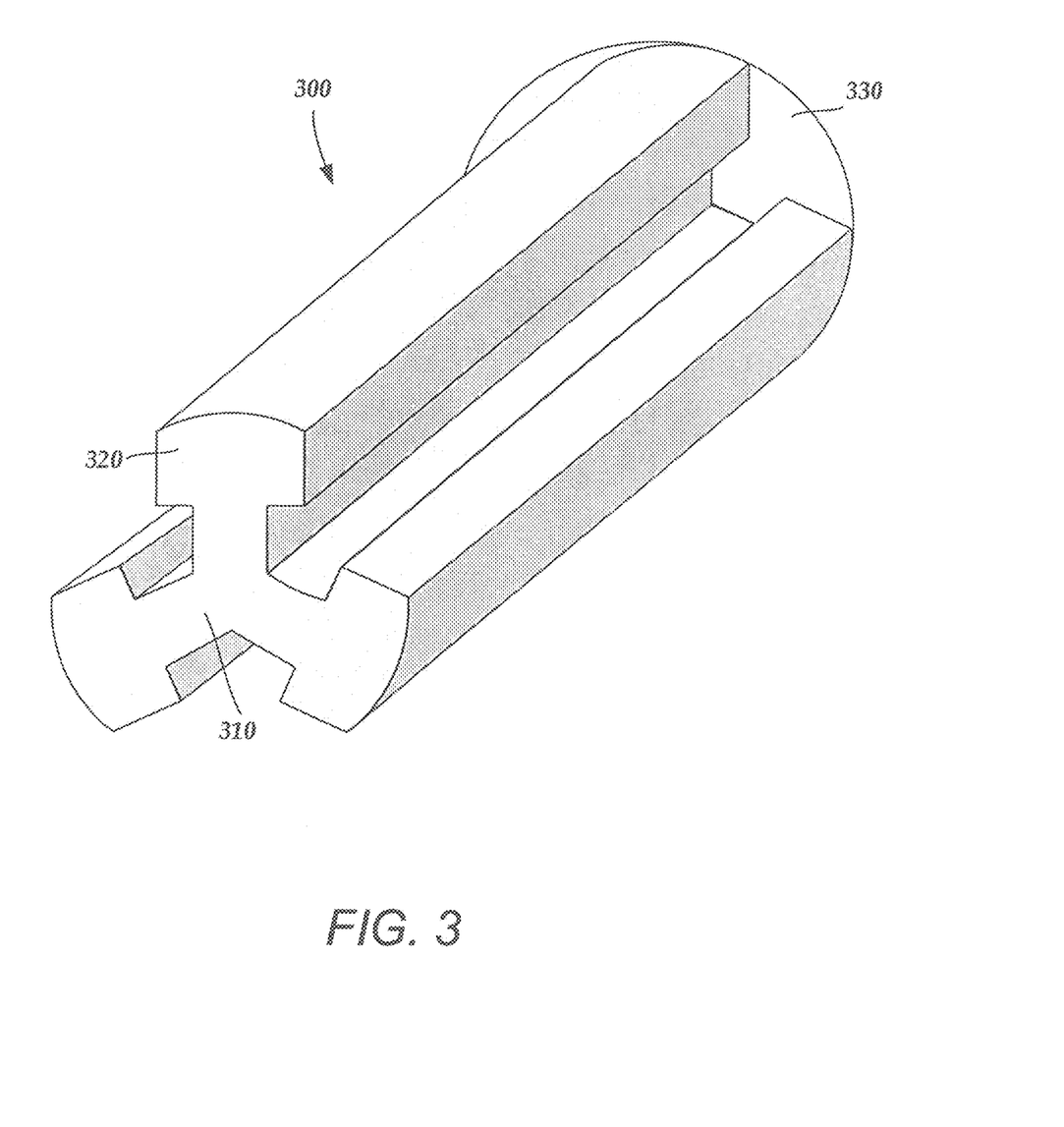
FIG. 3 is a schematic perspective view of one embodiment of a rail, according to the invention.

FIG. 3 is a schematic perspective view of one embodiment of a rail, according to the invention. The rail 300 may be formed of any suitable non-conductive material. In some embodiments, the rail 300 may include an elongate member that runs the length of the lead. In at least some other embodiments, the rail 300 is an elongate member that runs the length of a portion of the distal end of the lead where the segmented electrodes are to be attached. The rail may be coupled to the lead using any suitable method.

As seen in FIG. 3, the rail 300 includes prongs 310. In some embodiments, each prong 310 includes a member that projects from the center of the rail 300 and also runs along the length of the rail. As will be described in further detail below, the prongs 310 may be used to radially position the segmented electrodes about the rail. Though, FIG. 3 illustrates a rail 300 having three prongs 310, the rail 300 may include any number of prongs 310. For example, a rail 300 may include one, two, three, four, five, six, eight, ten or more prongs 310.

Each prong 310 may further include securing tabs 320 for securing a segmented electrode to the prong 310. In some embodiments, each prong 310 includes two securing tabs 320 in the shape of orthogonal arms. It will be understood that the securing tabs 320 may be in any shape that is suitable to secure the segmented electrodes to the prongs. For example, the securing tabs 320 may have a shape with a cross-section resembling curls, hooks, T-shapes, triangles, rectangles, squares, or hemispheres. Furthermore, any number of securing tabs 320 may be included in each prong 310. In some embodiments, each prong 310 will terminate with two securing tabs 320, one on either end of the prong 310. In some embodiments, the segmented electrodes may be attached, coupled or secured to the securing tabs 320 by sliding over the securing tabs 320.

The rail 300 may further be secured to a lead stop 330 at the proximal end of the rail 300. The lead stop 330 may serve as an end or stopper for the most distal segmented electrode or spacer. In some embodiments, the lead stop 330 may be disposed at the distal end of the lead. Thus, a segmented electrode or spacer may be slid or coupled to the prongs 310 and pushed along the length of the rail 300 until it contacts the lead stop 330.

Figure 4A:
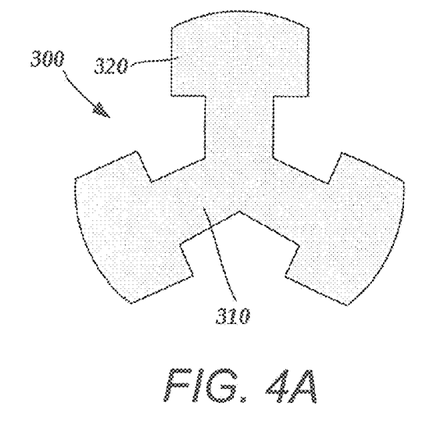
FIG. 4A is a schematic cross-sectional view of a first embodiment of a rail having three prongs, according to the invention.

As previously indicated, any number of prongs 310 may be included in the rail 300. FIG. 4A is a schematic cross-sectional view of a first embodiment of a rail 300 having three prongs 310. The cross-section of rail 300 corresponds to that of rail 300 described in FIG. 3. Because the rail 300 includes three prongs 310, up to three segmented electrodes may be coupled at each longitudinal level. Furthermore, as seen in FIG. 4A, the prongs 310 may be uniformly distributed about the rail 300 so that the angle between each prong 310 is the same. For example, in FIG. 4A the angle between each prong 310 is 120 degrees. Such a configuration will result in a radially segmented electrode array having segmented electrodes that are radially disposed 120 degrees apart. FIG. 4A also illustrates securing tabs 320, disposed at the end of each prong 310.

Figure 4B:
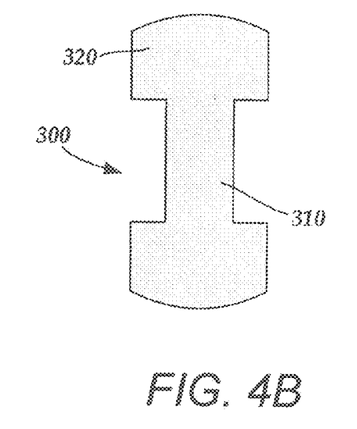
FIG. 4B is a schematic cross-sectional view of a second embodiment of a rail having two prongs, according to the invention.

FIG. 4B is a schematic cross-sectional view of a second embodiment of a rail 300 having two prongs 310. Though FIG. 4B illustrates two prongs 310 that are disposed 180 degrees apart, any angle between the two prongs 310 may be formed. For example, if the two prongs 310 are disposed 30 degrees apart, a V-shaped rail may be formed. For the purpose of discussion, the two-prong configuration shown in FIG. 4B may be referred to as the I-beam configuration. As seen in FIG. 4B, the rail 300 essentially includes two prongs 310 that are disposed end-to-end, so that they are joined. Essentially, the two prongs 310 may be said to create a single prong 310 having two pairs of securing tabs 320.

Figure 4C:
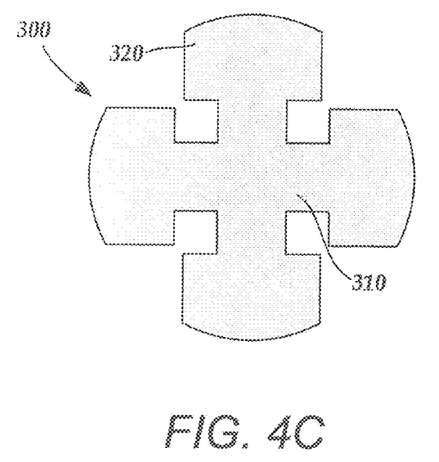
FIG. 4C is a schematic cross-sectional view of a third embodiment of a rail having four prongs, according to the invention.

FIG. 4C is a schematic cross-sectional view of a third embodiment of a rail 300 having four prongs 310. The four prongs 310 are uniformly distributed 90 degrees apart, with each prong 310 terminating in securing tabs 320. In at least some other embodiments, the prongs 310 are not uniformly distributed. The cruciform-shaped rail may be used to support up to four segmented electrodes at each level. Thus, the rail 300 of FIG. 4C may be used to support the 4-4 or a 4-4-4-4 configuration described above.

Figure 4D:
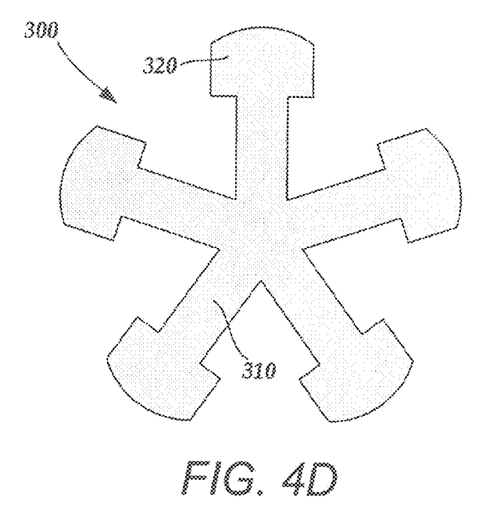
FIG. 4D is a schematic cross-sectional view of a fourth embodiment of a rail having five prongs, according to the invention.

FIG. 4D is a schematic cross-sectional view of a fourth embodiment of a rail 300 having five prongs 310. The rail 300 of FIG. 4D may support up to give segmented electrodes 500 at each longitudinal level. Furthermore, the prongs 310 may be uniformly distributed such that the angle between each prong 310 is 72 degrees. In at least some other embodiments, the prongs 310 are not uniformly distributed. FIGS. 4A-D are provided for the purpose of illustration only and it will be understood that the rail 300 may include any number of prongs 310 depending on the number of segmented electrodes desired at each longitudinal level of the lead.

Figure 5:
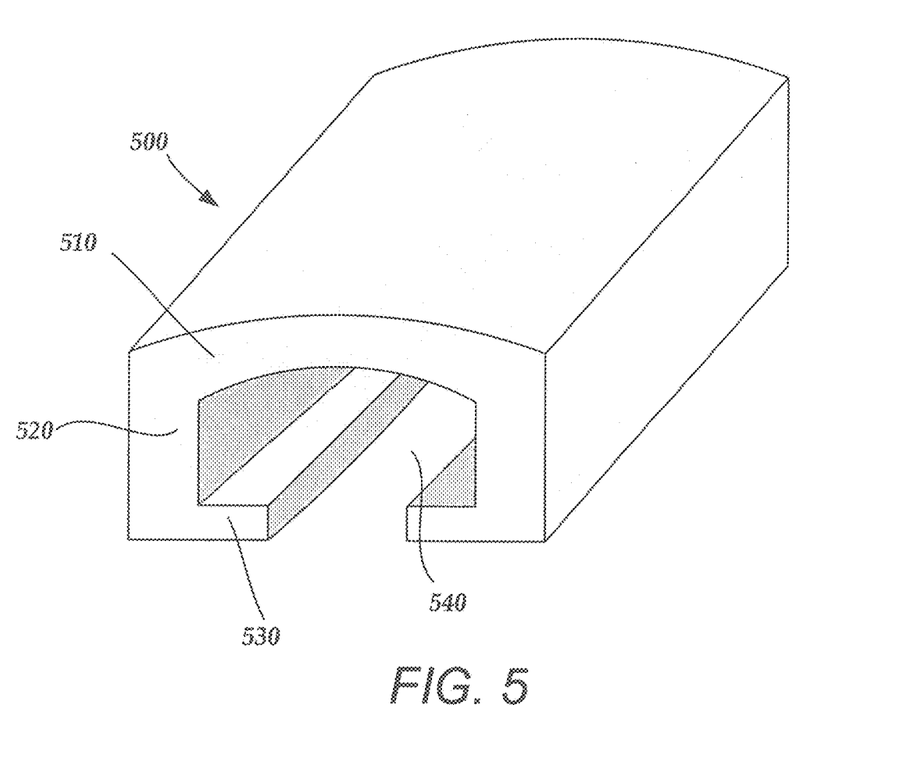
FIG. 5 is a schematic perspective view of one embodiment of a segmented electrode, according to the invention.

Segmented electrodes may be manufactured to couple with the prongs 310 of the rail 300. In some embodiments, the segmented electrodes are formed to have a passage in a shape that complements or corresponds to the prongs 310. FIG. 5 is a schematic perspective view of one embodiment of a segmented electrode 500. As can be appreciated from FIG. 5, the segmented electrode 500 includes a face 510, two arms 520 and two ridges 530.

The arms 520 of the segmented electrodes 500 may be formed in any length. In some embodiments, the arms 520 of the segmented electrodes 500 are long enough to house the securing tabs 320 of the rail 300. In some embodiments, each of the arms 520 of the segmented electrode 500 is the same length.

Ridges 530 may be disposed at the distal end of the arms 520. The two ridges 530 may be used to secure the segmented electrode 500 to a prong 310. The segmented electrode 500 may include any number of ridges 530 suitable for coupling the segmented electrode 500 to the prong 310. In some embodiments, a single ridge 530 may be sufficient to couple the segmented electrode 500 to the prong 310. In at least some other embodiments, two, three, four, five or six ridges 530 are used to couple the segmented electrode 500 to the prong 310. In embodiments having multiple ridges 530, more than one ridge 530 may be disposed on a single arm 520. For example, each arm 520 may terminate with one, two, three, or four ridges 530. Furthermore, the ridges 530 may be formed in different shapes. For example, FIG. 5 shows ridges 530 in the form of laterally projecting members. Alternatively, any type of ridge, such as a hook, a curl, a rib, rim or protrusion may be used to couple the segmented electrode 500 to the prong 310, particularly if the prong 310 or securing tabs 320 (or both) have corresponding shapes.

The segmented electrode 500 having ridges 530 forms a passage 540 on the inside of the segmented electrode 500. The passage 540 may be a cavity or lumen that longitudinally extends along the length of the segmented electrode 500. In some embodiments, the passage 540 is made to have a shape that corresponds to the securing tabs 320 of the prongs 310. It will be understood that the segmented electrodes 500 may have different shapes, ridges 530 and passages 540, depending on the desired arrangement of electrodes on the lead.

Figure 6A:
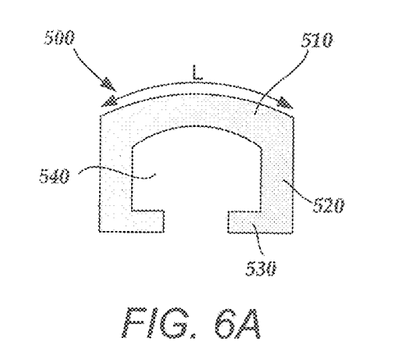
FIG. 6A is a schematic cross-sectional view of one embodiment of a segmented electrode, according to the invention.

FIG. 6A is a schematic cross-sectional view of one embodiment of a segmented electrode 500. In some embodiments, the segmented electrode 500 is made to have ridges 530 and a passage 540 that will correspond to the rail 300 of FIG. 4A. Thus, three segmented electrodes 510 may be disposed on the rail 300 to create a lead having up to three segmented electrodes at any given level. In some embodiments, the segmented electrode 500 is slid over the prongs 310 of the rail 300 from the distal end of the rail 300 to the desired position along the length of the rail 300. As can be appreciated by comparing FIGS. 4A and 6A, the cross-section of one prong 310 of the rail 300 of FIG. 4A corresponds or is complementary to the cross-section of the passage 540 of the segmented electrode 500.

Figure 6B:
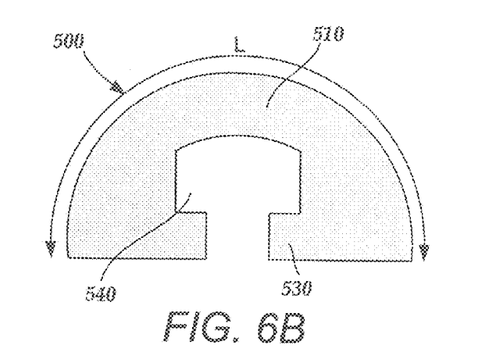
FIG. 6B is a schematic cross-sectional view of a second embodiment of a segmented electrode, according to the invention.

FIG. 6B is a schematic cross-sectional view of a second embodiment of a segmented electrode 500. The segmented electrode 500 of FIG. 6B may be used in conjunction with a number of rail configurations, for example those of FIGS. 4A and 4B. As in the segmented electrode 500 of FIG. 6A, the segmented electrode 500 of FIG. 6B includes ridges 530 and a passage 540 for coupling to the prongs 310 of a rail 300. When two segmented electrodes 500 are formed to have a cross-sectional hemispherical shape such as that of FIG. 6B, and coupled to an I-beam configuration of FIG. 4B, the result is a ring electrode at that longitudinal level. Thus, by changing the shape of the segmented electrode 500, both segmented and ring electrodes may be disposed on the lead.

Figure 6C:
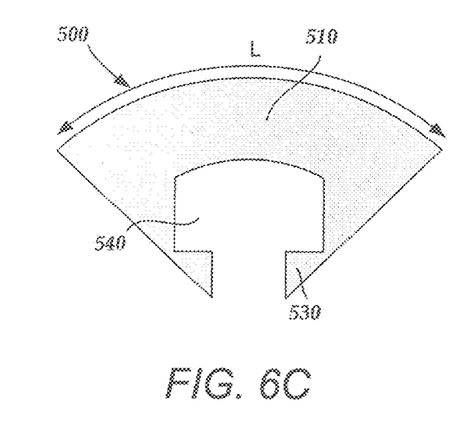
FIG. 6C is a schematic cross-sectional view of a third embodiment of a segmented electrode, according to the invention.
Figure 6D:
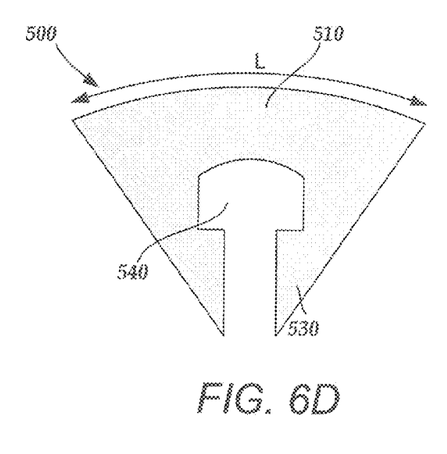
FIG. 6D is a schematic cross-sectional view of a fourth embodiment of a segmented electrode, according to the invention.

FIGS. 6C and 6D are schematic cross-sectional views of a third and a fourth embodiment of a segmented electrode 500. As can be appreciated from these figures, the cross-sectional shape of the segmented electrodes 500 may be modified to couple to different rail systems. For example, the segmented electrode 500 of FIG. 6C is formed to have a cross-sectional shape that will couple to rail systems having four or less prongs 310. Conversely, the segmented electrode 500 of FIG. 6D is narrower near the top so that it may be coupled to rail systems having two, three, four, or five prongs 310. As described herein, the narrowness of a segmented electrode 500 is defined by the arc length L of the outer edge of the segmented electrode. Thus, a segmented electrode 500 having a short arc length L may be suitable for rail configurations having multiple prongs 310 while a segmented electrode having a longer arc length L, such as that shown in FIG. 6B, may only be suitable for coupling to rails 300 having fewer prongs 310.

Figure 7A:
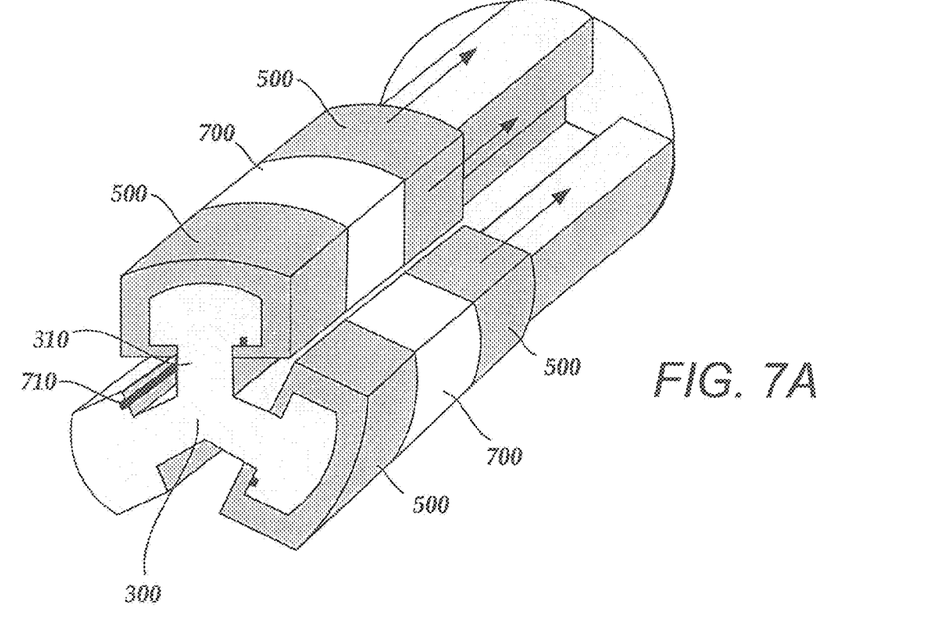
FIG. 7A is a schematic perspective view of one embodiment of a rail having segmented electrodes and a spacer, according to the invention.

FIG. 7A is a schematic perspective view of one embodiment of a rail 300 having a number of segmented electrodes 500 disposed on the rail. As seen in FIG. 7A, the segmented electrodes 500 may be slid or coupled to the prongs 310 from the distal end of the rail 300, and pushed along the length of the rail 300 in the direction of the arrows. The segmented electrodes 500 may be individually coupled to rail 300. Thus, in the rail 300 having three prongs 310, when three segmented electrodes 500 are slid, one over each prong 310, the result is one complete longitudinal level having three electrodes. In order to separate the different longitudinal levels of segmented electrodes, spacers 700 may also be slid along the rail 300.

In some embodiments, spacers 700 are disposed next to each segmented electrode 500 along the length of the rail 300. The spacers 700 may be disposed between the segmented electrode 500 and have a passage similar to that of the segmented electrodes 500 for coupling to the rail 300. The spacers 700 can be made of any non-conductive biocompatible material including, for example, silicone, polyurethane, and polyetheretherketone (PEEK). The spacers 700 help electrically isolate the segmented electrodes 500.

In some embodiments, three segmented electrodes 500 are disposed on the rail 300 having three prongs 310, one over each prong 310. The three segmented electrodes 500 are slid over the length of the rail 300. This creates one longitudinal level of segmented electrodes 500. Three spacers 700 may then be slid along the rail 300, one on each prong 310. This process may be repeated with alternating levels of segmented electrodes 500 and spacers 700 to form, for example, a 3-3-3-3 configuration.

Figure 7B:
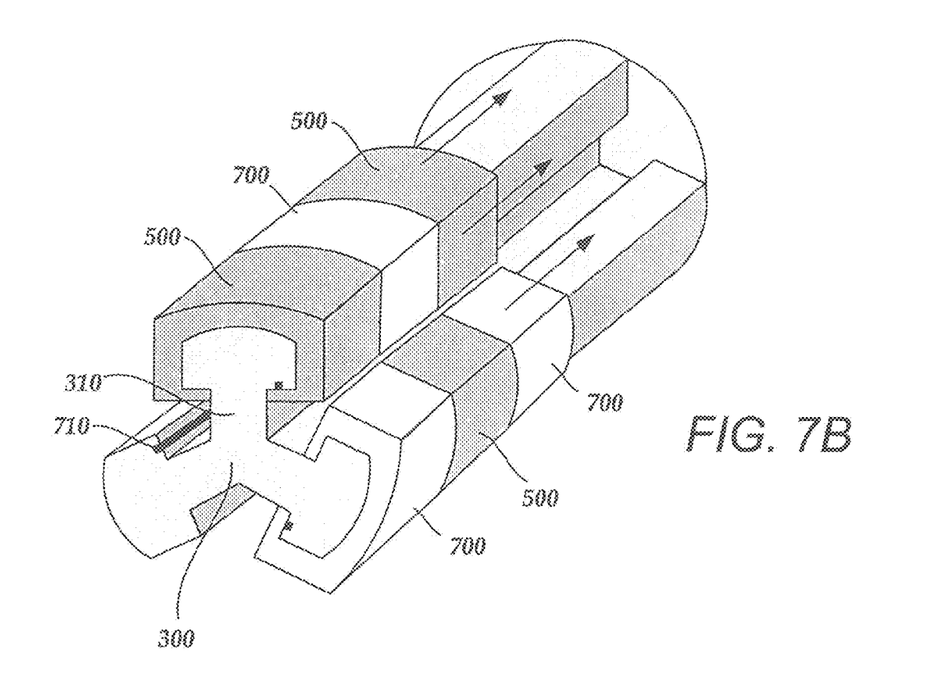
FIG. 7B is a schematic perspective view of another embodiment of a rail having segmented electrodes and spacers in a segmented orientation, according to the invention.

As seen in FIG. 7A, the spacers 700 may be the same length as the segmented electrode 500. In at least some other embodiments, the spacers 700 and the segmented electrodes 500 are of different lengths. As previously described with respect to FIG. 1B, the plurality of segmented electrodes 500 may also be arranged in different orientations relative to each other, in a so-called "staggered arrangement" as shown in FIG. 7B. Having spacers 700 and segmented electrodes 500 of the same length can be particularly useful when forming a lead having a staggered segmented electrode arrangement.

Using a rail 300 and spacers 700, a staggered segmented electrode arrangement may be formed. For example, in a rail 300 having three prongs 310, a segmented electrode 500 may be disposed on the first prong 130. On the second and third prongs 310, two spacers 700 may be disposed, one on each. The result is a longitudinal level having a segmented electrode 500 on the first prong 310, and spacers 700 on the second and third prongs 310. This longitudinal level may simply be described as E-S-S, where the first "E" refers to a segmented electrode 500 on the first prong 310, and the second "S" and third "S" refer to spacers 700 on the second and third prongs 310. Again, using the shorthand notation, on a second longitudinal level, the electrode-spacer arrangement may be S-E-S. Then, on a third level the arrangement may be S-S-E. The result is a lead having a staggered orientation. It will be understood that this method can be used for a rail 300 having any number of prongs 310.

As previously noted, conductors attach to or from the segmented electrodes 500. The conductors 710 may be positioned and configured in a variety of ways. In some embodiments, each segmented electrode 500 is coupled to a single, independent conductor 710. In at least some other embodiments, a conductor 710 is coupled to multiple segmented electrodes 500. The conductors 710 may extend along the surface of the rail 300 or disposed on one of the prongs 310 or between one of the prongs 310 or any other suitable conductor arrangement. For example, the conductor 710 may be disposed along a surface of the prong 310 or along the surface of the securing tabs 320. Additionally, the conductors 710 may extend within the center of the rail 300 or within one of the prongs 310 and surface from within the structure at a predetermined longitudinal position where the segmented electrodes 500 will be located. Furthermore, it will be understood that a combination of these configurations may be utilized within a single embodiment.

Figure 8:
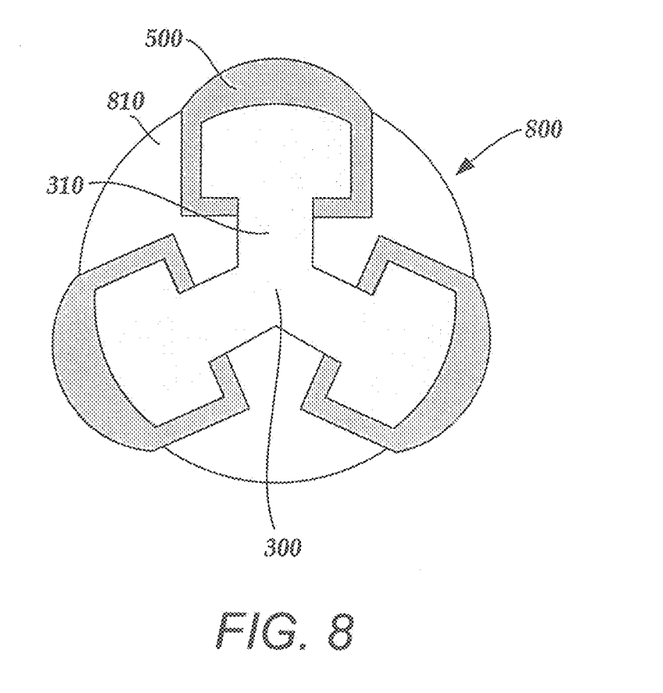
FIG. 8 is a schematic cross-sectional view of one embodiment of a lead having segmented electrodes before grinding, according to the invention.

FIG. 8 is a schematic cross-sectional view of one embodiment of a lead 800 having segmented electrodes 500 disposed over a rail 300. Once the segmented electrodes 500 and the spacers 700 have been properly positioned on the prongs 310 of the rail 300, a lead body 810 may be formed. The lead body 810 may be formed of a biocompatible, non-conducting material. In some embodiments, the lead body 810 may be formed by backfilling any space not occupied by the rail 300, the segmented electrode 500, and the spacers. However, it will be understood that the components of the lead may be coupled in any order. For example, in at least some other embodiments, the lead body 810 is formed over the rail 300 and the segmented electrodes 500 and spacers are then coupled to the rail 300.

As can be appreciated from FIG. 8, the lead 800 includes segmented electrodes that outwardly project to a diameter greater than that of the lead body 810. Thus, in order to create an isodiametric lead, the segmented electrodes 500, spacers 700 and lead body 810 may be ground down to the same level.

Figure 9:
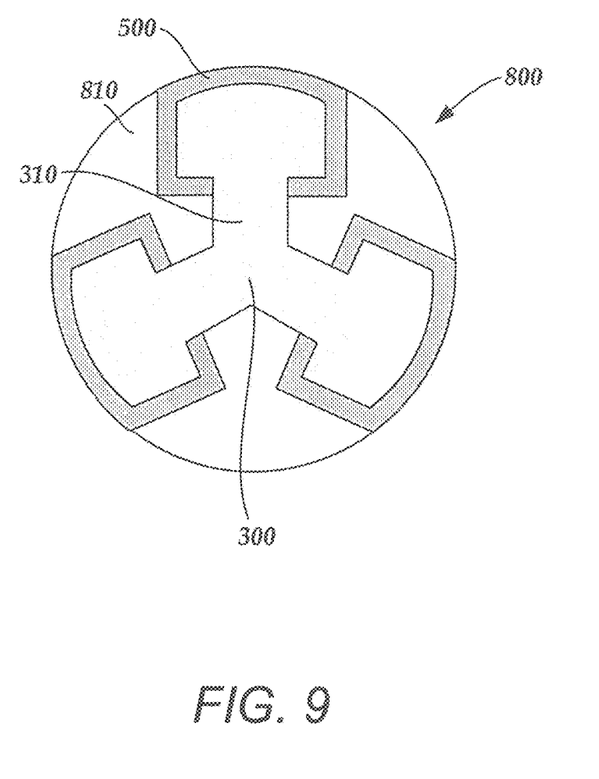
FIG. 9 is a schematic cross-sectional view of the lead of FIG. 8 after grinding, according to the invention.

FIG. 9 is a schematic cross-sectional view of the lead of FIG. 8 after grinding of the segmented electrodes 500. In some embodiments, it may be useful or desirable to grind down the segmented electrodes 500 and the spacers (not shown) to an appropriate diameter. After the segmented electrodes 500 and spacers have been ground down to the same level as the lead body 810, the lead 800 is isodiametric, having substantially the same diameter at all points. The result is a substantially cylindrical lead 800 that is suitable for deep brain stimulation.

Modifications of these methods are possible. For example, two or more of these methods may be used in combination to provide a rail having multiple prongs that are configured differently. Furthermore, by varying the prongs and securing tabs, it may be possible to indicate the type of electrode that will be coupled to each prong. In some embodiments, these methods are used with lead constructions other than deep brain stimulation leads.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A device for electrical stimulation, comprising:
   a lead having a longitudinal surface and a distal end, the lead comprising:
   a longitudinal rail disposed within the distal end of the lead and comprising a central portion and at least two prongs extending radially away from the central portion, each prong being configured and arranged to receive at least one segmented electrode; and
   a plurality of segmented electrodes disposed along the longitudinal surface of the lead near the distal end of the lead, wherein each of the plurality of segmented electrodes receives a first portion of a one of the at least two prongs so that the segmented electrode is disposed on top of the one of the at least two prongs, wherein each of the plurality of segmented electrodes comprises a securement portion that extends underneath part of the first portion of the one of the at least two prongs received by the segmented electrode to facilitate securement of the segmented electrode to the one of the at least two prongs.

2. The device of claim 1, wherein the at least two prongs are uniformly spaced around the circumference of the rail.

3. The device of claim 1, wherein the longitudinal rail comprises exactly three or four prongs.

4. The device of claim 1, wherein the first portion of the one of the at least two prongs received by at least one of the segmented electrodes is bounded on at least three sides by the segmented electrode.

5. The device of claim 1, wherein at least two of the segmented electrodes are disposed on top of a same one of the at least two prongs.

6. The device of claim 5, further comprising a spacer, wherein the spacer receives a portion of the same one of the at least two prongs so that the spacer is disposed on top of the same one of the at least two prongs and between the at least two of the segmented electrodes disposed on the same one of the at least two prongs.

7. The device of claim 1, further comprising a lead body, at least a portion of the lead body at least partially disposed in voids between the plurality of segmented electrodes.

8. The device of claim 1, wherein the at least two prongs are configured and arranged such that the plurality of segmented electrodes are uniformly radially arranged around the circumference of the rail.

9. The device of claim 1, wherein each of the at least two prongs comprises at least one securing tab as part of the first portion received within the segmented electrodes.

10. The device of claim 9, wherein each of the plurality of segmented electrodes defines a cavity having a cross-sectional shape corresponding to the at least one securing tab.

11. An implantable stimulation system, comprising:
the device of claim 1; and
a control module coupleable to the lead.

12. A device for electrical stimulation, comprising:
a lead having a longitudinal surface and a distal end, the lead comprising:
a longitudinal rail disposed within the distal end of the lead and comprising a central portion and at least two prongs, including a first prong, extending radially away from the central portion, each prong being configured and arranged to receive a plurality of segmented electrodes; and
a plurality of segmented electrodes, including a first segmented electrode and a second segmented electrode, disposed along the longitudinal surface of the lead near the distal end of the lead, the first and second segmented electrodes each comprising a bottom surface and defining a cavity open at the bottom surface, the first segmented electrode receiving a first portion of the first prong within the cavity of the first segmented electrode so that the first segmented electrode is disposed on top of the first prong, the second segmented electrode receiving a second portion of the first prong within the cavity of the second segmented electrode so that the second segmented electrode is disposed on top of the first prong, wherein each of the first and second segmented electrodes comprises a securement portion that extends underneath part of the first or second portion, respectively, of the first prong to facilitate securement of the first and second segmented electrodes to the first prong.

13. The device of claim 12, wherein the plurality of segmented electrodes are disposed at predetermined longitudinal levels along a length of the rail.

14. The device of claim 12, further comprising a spacer disposed between the first and second segmented electrodes and disposed on top of the first prong.

15. The device of claim 12, further comprising a lead body, at least a portion of the lead body being disposed between the plurality of segmented electrodes.

16. An implantable stimulation system, comprising:
the device of claim 12; and
a control module coupleable to the lead.

17. The implantable stimulation system of claim 16, wherein the implantable stimulation system is a deep brain stimulator.

18. A method of manufacturing the device of claim 12, the method comprising:
sliding the first segmented electrode onto the first prong of the rail;
disposing a spacer adjacent to first segmented electrode and over the first prong of the rail;
sliding the second segmented electrode onto the first prong of the rail and adjacent to the spacer so that the spacer is positioned between the first and second segmented electrodes; and
forming a substantially cylindrical lead body, the substantially cylindrical lead body b configured to at least partially surround the longitudinal rail and the plurality of segmented electrodes.

19. The method of claim 18, further comprising grinding the plurality of segmented electrodes and the spacer so that the lead is isodiametric.

20. The method of claim 18, wherein disposing the spacer comprises sliding the spacer onto the first prong of the rail.

\* \* \* \* \*